(12) United States Patent
Gourineni

(10) Patent No.: US 9,682,003 B2
(45) Date of Patent: Jun. 20, 2017

(54) ACHILLES STRETCHING DEVICES AND METHODS PERFORMED THEREWITH

(71) Applicant: Prasad Gourineni, Oak Brook, IL (US)

(72) Inventor: Prasad Gourineni, Oak Brook, IL (US)

( * ) Notice: Subject to any disclaimer, the term of this patent is extended or adjusted under 35 U.S.C. 154(b) by 242 days.

(21) Appl. No.: 14/337,670

(22) Filed: Jul. 22, 2014

(65) Prior Publication Data

US 2014/0336012 A1 Nov. 13, 2014

Related U.S. Application Data

(63) Continuation-in-part of application No. 13/024,585, filed on Feb. 10, 2011, now abandoned, which is a
(Continued)

(51) Int. Cl.
*A61F 5/14* (2006.01)
*A61H 1/00* (2006.01)
(Continued)

(52) U.S. Cl.
CPC ........... *A61H 1/0266* (2013.01); *A43B 7/142* (2013.01); *A43B 7/145* (2013.01); *A43B 7/1425* (2013.01); *A43B 7/1435* (2013.01); *A43B 7/1445* (2013.01); *A43B 7/223* (2013.01); *A43B 13/148* (2013.01); *A43B 17/023* (2013.01); *A61F 5/14* (2013.01); *A61H 39/04* (2013.01); *A61H 2201/1253* (2013.01);
(Continued)

(58) Field of Classification Search
CPC ......... A61F 5/14; A61H 1/0266; A61H 39/04; A61H 2201/1675; A61H 2201/1685; A61H 2201/165; A61H 2201/1284; A61H 2201/1642; A61H 2201/1253; A61H 2201/0107; A43B 7/14; A43B 7/1445; A43B 7/1435; A43B 7/1425; A43B 7/145; A43B 7/142; A43B 17/03; A43B 13/148
USPC ...... 601/28; 36/91, 141, 145, 150, 155, 160, 36/161–165, 170, 172; 482/79
See application file for complete search history.

(56) References Cited

U.S. PATENT DOCUMENTS

| | | | | |
|---|---|---|---|---|
| 1,145,533 A | * | 7/1915 | Wetmore | A43B 17/03 36/153 |
| 1,375,314 A | * | 4/1921 | Overton | A61H 7/001 601/27 |

(Continued)

*Primary Examiner* — Khoa Huynh
*Assistant Examiner* — Katharine Gracz
(74) *Attorney, Agent, or Firm* — Harness, Dickey & Pierce, P.L.C.

(57) ABSTRACT

Therapeutic devices and methods stretching the Achilles tendon. Each device includes base and wedge portions. The wedge portion has heel and toe ends, inside-foot and outside-foot edges, and an upper surface that includes a planar surface portion that lies in a wedge plane and an arcuate surface portion defined by a projection that extends out of the wedge plane. The wedge plane has a nonuniform elevation relative to the base portion as a result of the wedge portion having a fore-aft taper in the fore-aft direction and a lateral taper in the lateral direction. The fore-aft taper and the lateral taper are sufficient so that placement of a user's foot on the upper surface of the wedge portion causes supination and locking of the foot and enables stretching of the Achilles complex, while the arch of the user's foot is against and supported by the arcuate surface portion.

8 Claims, 12 Drawing Sheets

Related U.S. Application Data continuation-in-part of application No. 12/750,754, filed on Mar. 31, 2010, now abandoned.

(60) Provisional application No. 61/164,975, filed on Mar. 31, 2009.

(51) Int. Cl.

| | | |
|---|---|---|
| *A63B 23/08* | (2006.01) | |
| *A61H 1/02* | (2006.01) | |
| *A43B 7/14* | (2006.01) | |
| *A43B 7/22* | (2006.01) | |
| *A43B 13/14* | (2006.01) | |
| *A43B 17/02* | (2006.01) | |
| *A61H 39/04* | (2006.01) | |

(52) U.S. Cl.
CPC ............... *A61H 2201/1284* (2013.01); *A61H 2201/165* (2013.01); *A61H 2201/1642* (2013.01); *A61H 2201/1685* (2013.01); *A61H 2201/1695* (2013.01)

(56) References Cited

U.S. PATENT DOCUMENTS

| | | | | |
|---|---|---|---|---|
| 1,546,506 A * | 7/1925 | Naysmith | A61H 1/0266 482/79 |
| 1,818,683 A * | 8/1931 | Bischoff | A43B 7/14 36/163 |
| 1,981,379 A * | 11/1934 | Thomson | A63B 23/10 482/51 |
| 2,016,930 A * | 10/1935 | McCahan | A61H 1/0266 601/27 |
| 2,041,693 A * | 5/1936 | Boltz | A61H 15/0078 482/80 |
| 2,518,649 A * | 8/1950 | Tydings | A43B 3/128 36/11.5 |
| 2,554,718 A * | 5/1951 | Oleskey | A43B 7/1465 36/143 |
| 2,760,279 A * | 8/1956 | Jones | A43B 3/103 36/11.5 |
| 2,769,252 A * | 11/1956 | Monier | A43B 13/143 36/140 |
| 3,472,508 A * | 10/1969 | Baker | A63B 21/0004 36/83 |
| 3,595,244 A * | 7/1971 | Kugler | A43B 7/146 36/11.5 |
| 3,626,933 A * | 12/1971 | Pollock | A61H 39/04 601/104 |
| 3,859,727 A * | 1/1975 | Nakamoto | A43B 7/146 36/11.5 |
| 3,885,555 A * | 5/1975 | Nobbs | A43B 7/146 601/28 |
| 4,095,353 A * | 6/1978 | Foldes | A43B 13/38 36/11.5 |
| 4,573,678 A * | 3/1986 | Lamb | A63B 23/085 482/80 |
| 4,578,882 A * | 4/1986 | Talarico, II | A43B 13/14 36/103 |
| D337,876 S * | 8/1993 | Kilbey | D2/957 |
| 5,368,536 A * | 11/1994 | Stodgell | A63B 21/00072 482/123 |
| 5,537,764 A * | 7/1996 | Prahl | A61F 13/043 36/11.5 |
| 5,752,329 A * | 5/1998 | Horibata | A63B 25/10 36/141 |
| 5,827,205 A * | 10/1998 | Iwamoto | A61H 23/0218 601/111 |
| 6,063,013 A * | 5/2000 | Vathappallil | A63B 21/023 482/120 |
| 6,244,992 B1 * | 6/2001 | James | A61H 1/0237 482/19 |
| 6,267,742 B1 * | 7/2001 | Krivosha | A61F 5/0585 128/882 |
| 7,101,344 B1 * | 9/2006 | Wu | A61H 7/001 441/129 |
| 7,392,604 B2 * | 7/2008 | Greene | A43B 3/24 36/25 R |
| 2002/0183662 A1 * | 12/2002 | Lu | A61H 1/003 601/28 |
| 2002/0183664 A1 * | 12/2002 | Lu | A61H 1/0266 601/46 |
| 2003/0225348 A1 * | 12/2003 | Chen | A61H 1/005 601/28 |
| 2004/0023764 A1 * | 2/2004 | Repking | A63B 22/16 482/142 |
| 2005/0246924 A1 * | 11/2005 | Masoodifar | A43B 13/148 36/132 |
| 2006/0059726 A1 * | 3/2006 | Song | A43B 7/142 36/142 |
| 2006/0064048 A1 * | 3/2006 | Stano | A61F 5/0127 602/28 |
| 2006/0100557 A1 * | 5/2006 | Huang | A61H 15/0078 601/28 |
| 2006/0130364 A1 * | 6/2006 | Greene | A43B 3/24 36/28 |
| 2006/0276308 A1 * | 12/2006 | Wang | A63B 23/08 482/79 |
| 2010/0050471 A1 * | 3/2010 | Kim | A43B 7/081 36/29 |
| 2011/0054368 A1 * | 3/2011 | Sanders | A61H 1/0266 601/118 |
| 2011/0289798 A1 * | 12/2011 | Jung | A43B 7/142 36/91 |
| 2012/0232446 A1 * | 9/2012 | Ormsbee D.C., Dabco | A61H 7/001 601/134 |

* cited by examiner

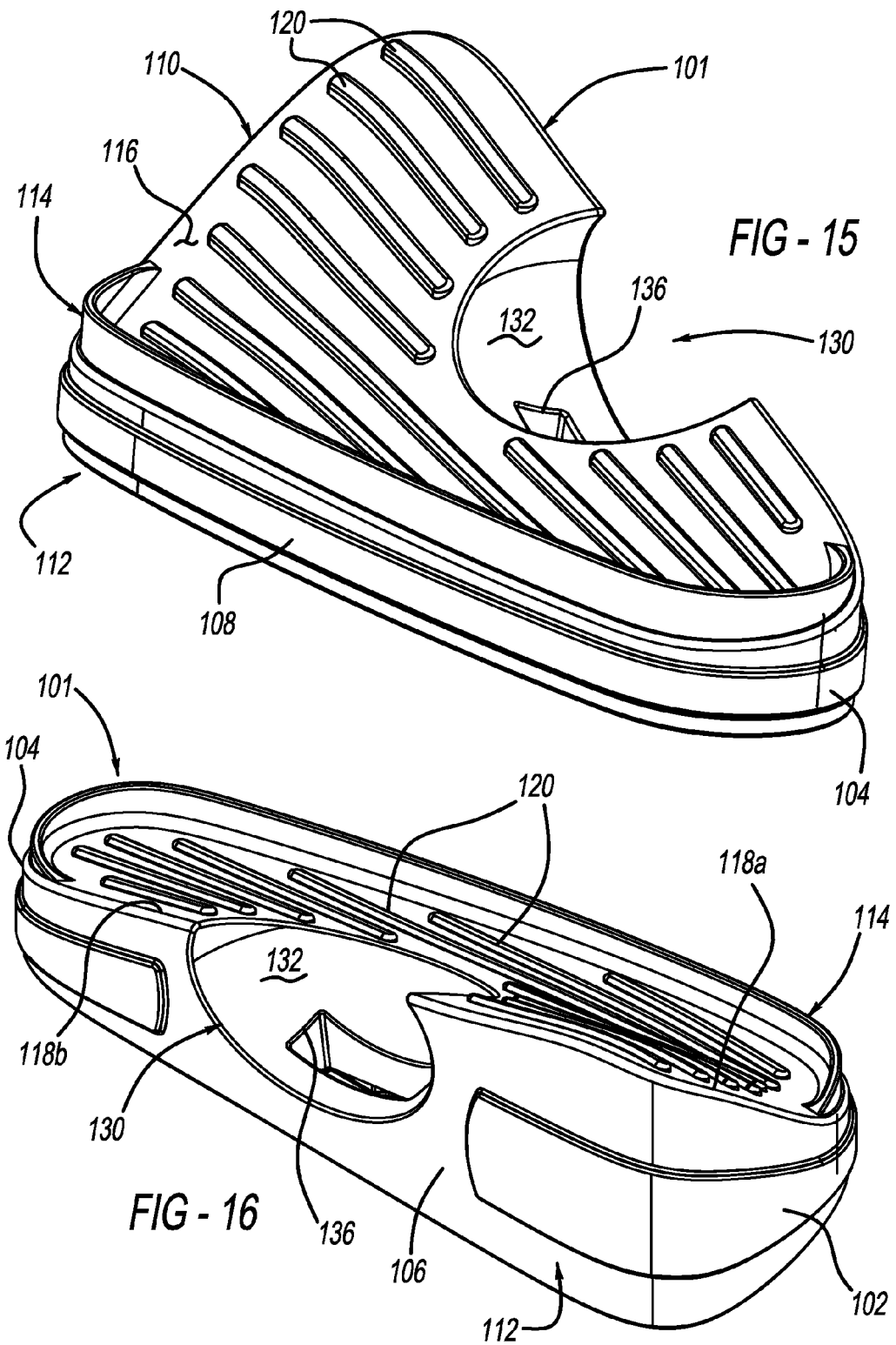

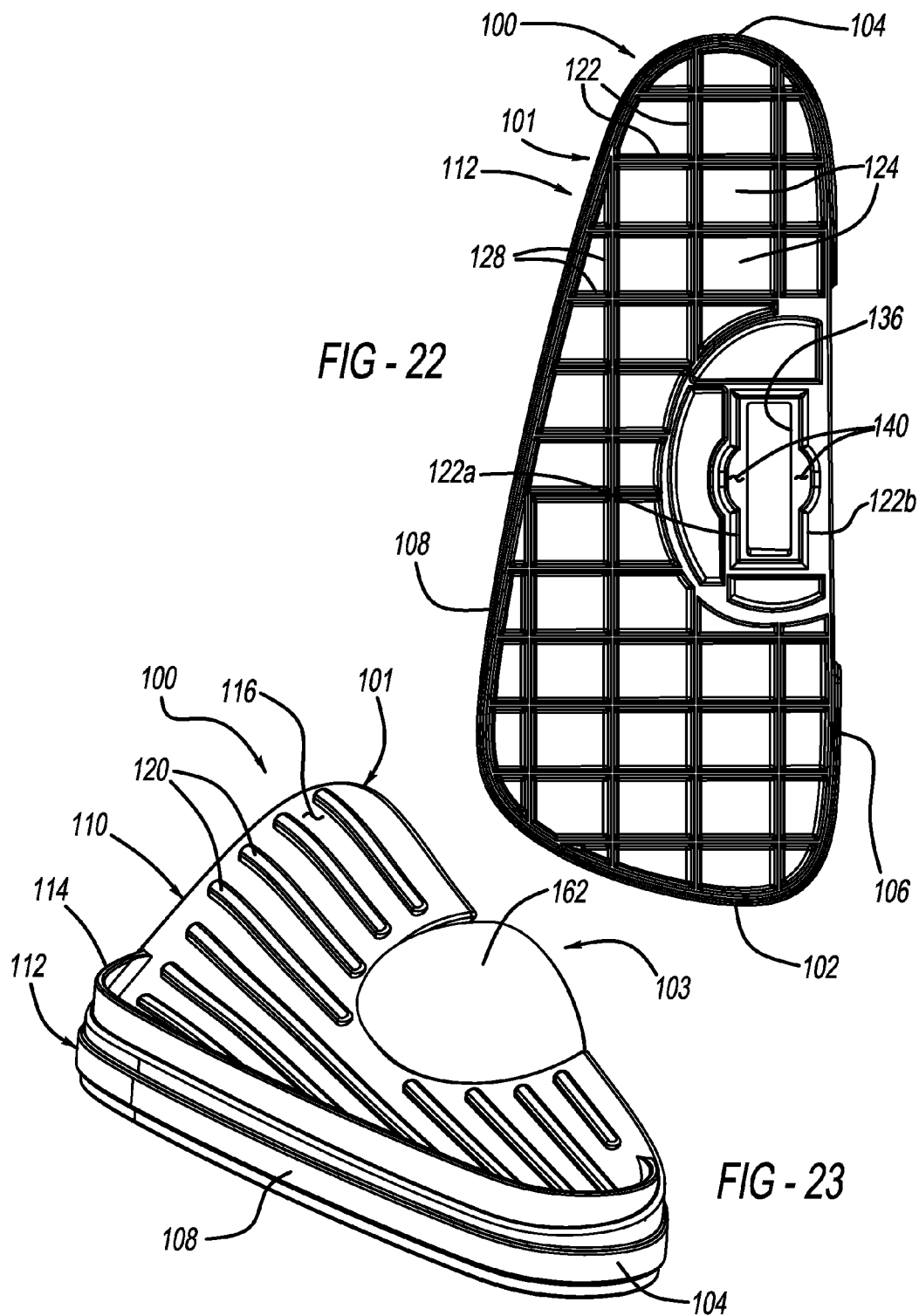

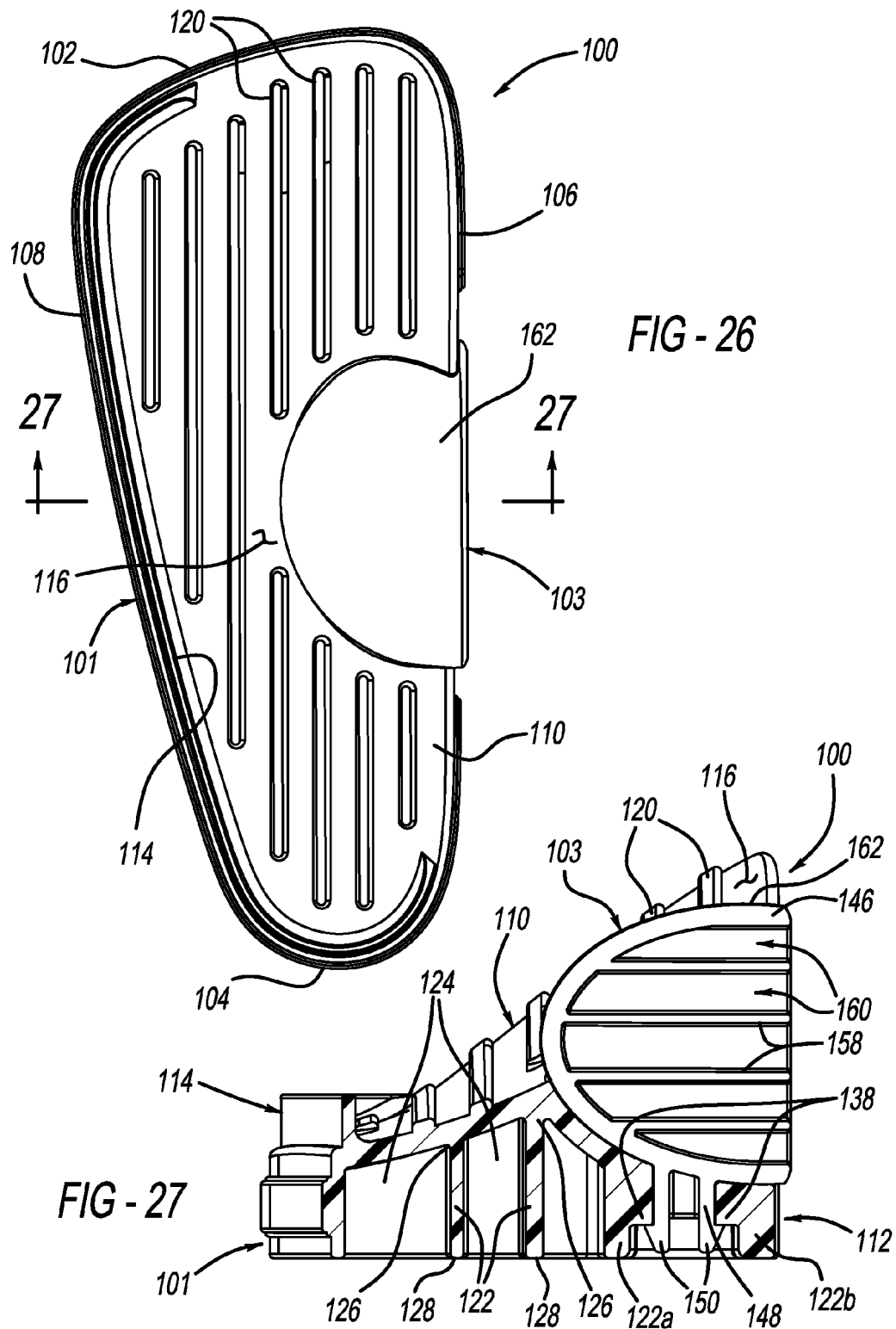

ACHILLES STRETCHING DEVICES AND METHODS PERFORMED THEREWITH

CROSS-REFERENCE TO RELATED APPLICATIONS

This application is a continuation-in-part of U.S. patent application Ser. No. 13/024,585 filed on Feb. 10, 2011, which is a continuation-in-part of U.S. patent application Ser. No. 12/750,754 filed on Mar. 31, 2010, which claims the benefit of U.S. Provisional Application No. 61/164,975, filed on Mar. 31, 2009. The entire disclosure of each of the above applications is incorporated herein by reference.

BACKGROUND

This section provides background information related to the present disclosure which is not necessarily prior art.

The present invention generally relates to therapy and physical fitness equipment, and more particularly to devices capable of stretching the calf muscle-Achilles tendon unit.

The Achilles tendon connects the calf muscles to the heel of the foot. The calf muscles pull on the heel through the Achilles tendon, enabling propulsion of the human body through the foot for walking and jumping activities. The combined length of the calf muscles and Achilles tendon should be short enough to contract strongly and generate enough power for daily activities, and also permit sufficient stretching to allow about ten to twenty degrees of ankle dorsiflexion. If the calf muscles and Achilles tendon cannot stretch and allow ankle dorsiflexion to this extent, the midfoot and the forefoot see abnormal stresses leading to pain and conditions like plantar fasciitis, flat feet, posterior tibial tendon dysfunction, stress fracture, and arthritis.

The normal human foot is a dynamic structure that can function as a flexible unit capable of adapting to uneven support surfaces during weight bearing, as well as a rigid unit capable of forward propulsion through tightening of the calf muscles. The loosening and stiffening of the foot automatically occur as a result of locking and unlocking the midfoot during walking and running. The same mechanism can be used in a reverse fashion to lock the midfoot and stiffen the foot by maximally lifting the big toe (hallux) and its metatarsal bone away from the ground or the level of the fifth toe and its metatarsal bone (supination of the forefoot). One can also pronate the forefoot by elevating the fifth metatarsal relative to the first metatarsal, which results in unlocking the foot and stretching the arch of the foot.

The Achilles tendon can be stretched by daily activities and specific exercises that force the forefoot (toes and metatarsus) toward the leg. In adults, weight-bearing exercises are generally more useful for stretching the Achilles tendon, whereas in children stretching is typically best accomplished with the assistance of an adult. Dynamic splints that provide constant stretching of the tendon can be used by both adults and children. However, such devices achieve limited stretching of the Achilles tendon because stretching of the calf muscle-Achilles tendon unit is more effective if the foot acts as a rigid lever and transmits all the stretch to the Achilles. If the foot is not rigid, some of the stretching forces tend to stretch the arch of the foot and can create or worsen an existing flatfoot condition.

SUMMARY

This section provides a general summary of the disclosure, and is not a comprehensive disclosure of its full scope or all of its features.

The present invention provides therapeutic devices and methods suitable for stretching the Achilles tendon. The devices provide for supination of the forefoot to make the foot more rigid and allow better stretching of the calf muscle-Achilles unit. Furthermore, the devices provide support for the arch of the foot, reducing stretching forces that would tend to stretch the arch of the foot and create or worsen an existing flatfoot condition.

According to a first aspect of the invention, a therapeutic device is provided that comprises a wedge portion and a base portion. The wedge portion has oppositely-disposed heel and toe ends in a fore-aft direction of the wedge portion, oppositely-disposed inside-foot and outside-foot edges in a lateral direction of the wedge portion, and an upper surface delineated by the heel and toe ends and the inside-foot and outside-foot edges of the wedge portion. The upper surface of the wedge portion comprises a planar surface portion that lies in a wedge plane and an arcuate surface portion defined by a projection that extends out of the wedge plane. The wedge plane has a nonuniform elevation relative to the base portion as a result of the wedge portion having a fore-aft taper in the fore-aft direction and a lateral taper in the lateral direction, wherein the inside-foot edge has a higher elevation at the toe end than at the heel end and the outside-foot edge has a substantially constant elevation in the fore-aft direction. The fore-aft taper and the lateral taper are sufficient so that placement of a user's heel on the upper surface at the heel end and the user's toes on the upper surface at the toe end causes supination and locking of the foot and enables stretching of the Achilles complex. The projection extends from the inside-foot edge toward but not to the outside-foot edge in the lateral direction, and extends between but not to the toe and heel ends of the wedge portion. The arcuate surface portion of the projection has arcuate contours in both the lateral and fore-aft directions, and the arcuate contours of the arcuate surface portion define an apex that is at least ten millimeters to about forty millimeters from the wedge plane.

According to further aspects of the invention, the device can be configured as a freestanding structure, in other words, the device does not require any additional external structure to support the device or enable the device to perform its intended function of supination and locking of the foot during stretching of the Achilles complex. As such, the base portion is adapted for placement on a surface of a floor or ground and the wedge portion enables weight-bearing stretching of the Achilles complex. The device can also be configured as a shoe wherein the wedge portion causes weight-bearing stretching of the Achilles complex when the user walks and runs while wearing the shoe, or configured as a splint wherein the nonuniform elevation of the upper surface of the wedge portion relative to the base portion is a result of the splint twisting the wedge portion, or configured as an apparatus comprising at least one strap attached to the base portion so that a user can pull the wedge portion to cause stretching of the Achilles complex.

Other aspects of the invention include stretching techniques using the devices described above. In each case, the device is specifically configured for stretching the Achilles complex of one foot, yet can also be switched to the opposite foot to pronate that foot and stretch the arch of the foot, for example, as a therapeutic treatment for high arched feet.

A technical effect of the invention is the ability of the devices to achieve greater stretching of the calf muscle-Achilles tendon unit as a result of the devices causing supination and locking of the foot, which results in the foot acting as a rigid lever that transmits essentially all of a stretching motion to the Achilles tendon. In this manner, the effectiveness of the stretching technique is increased to promote the ability of the calf muscles and Achilles tendon to stretch and allow ankle dorsiflexion, thereby reducing abnormal stresses within the midfoot and forefoot. Furthermore, the projection minimizes if not avoids stretching of the arch of the foot, thereby avoiding the creation or worsening of a flatfoot condition.

Other aspects and advantages of this invention will be better appreciated from the following detailed description. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 15 is a perspective view of a therapeutic device in accordance with the principles of the present disclosure.

FIG. 16 is another perspective view of the therapeutic device of FIG. 15.

FIG. 22 is a bottom view of the therapeutic device of FIG. 15.

FIG. 23 is a perspective view of the therapeutic device of FIG. 15, including an insert in accordance with the principles of the present disclosure.

FIG. 26 is a top view of the therapeutic device of FIG. 23.

FIG. 27 is a cross-sectional view of the therapeutic device of FIG. 23 taken along the line 27-27 of FIG. 26.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The Figures depict therapeutic devices that can be used to stretch the Achilles tendon in accordance with particular embodiments of the invention. For convenience, consistent reference numbers are used throughout the Figures to identify the same or functionally equivalent elements. Furthermore, to facilitate the description of the devices, the terms "fore," "aft," "side," "upper," "lower," "right," "left," etc., will be used in reference to the perspective of a user during use of the devices, and therefore are relative terms and should not be otherwise interpreted as limitations to the construction of the devices or as limiting the scope of the invention.

Figure 1:
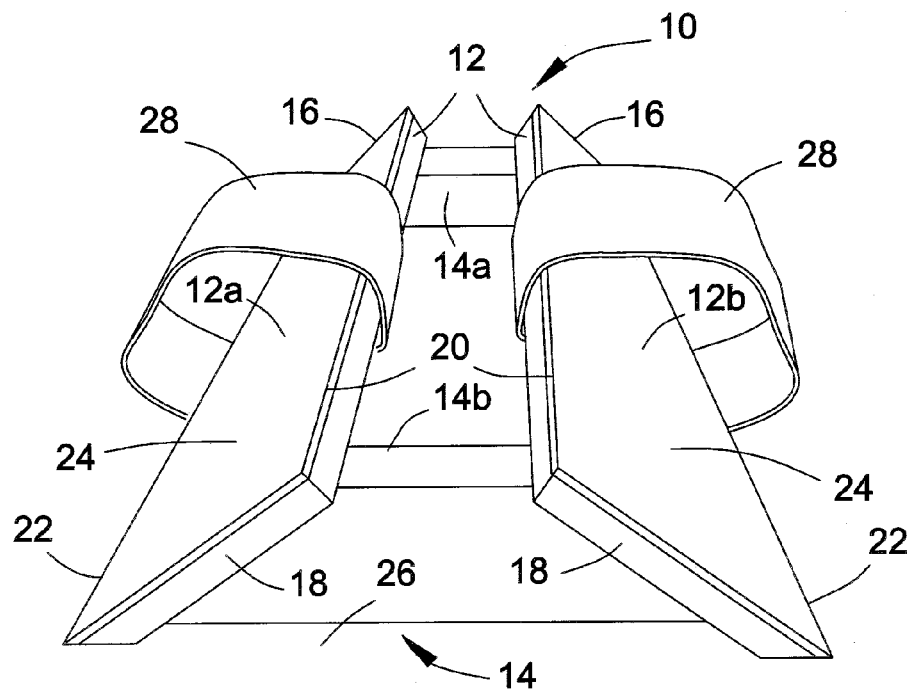
FIGS. 1 and 2 are end and side views, respectively, of a freestanding Achilles tendon stretching device in accordance with a first embodiment of this invention.
Figure 2:
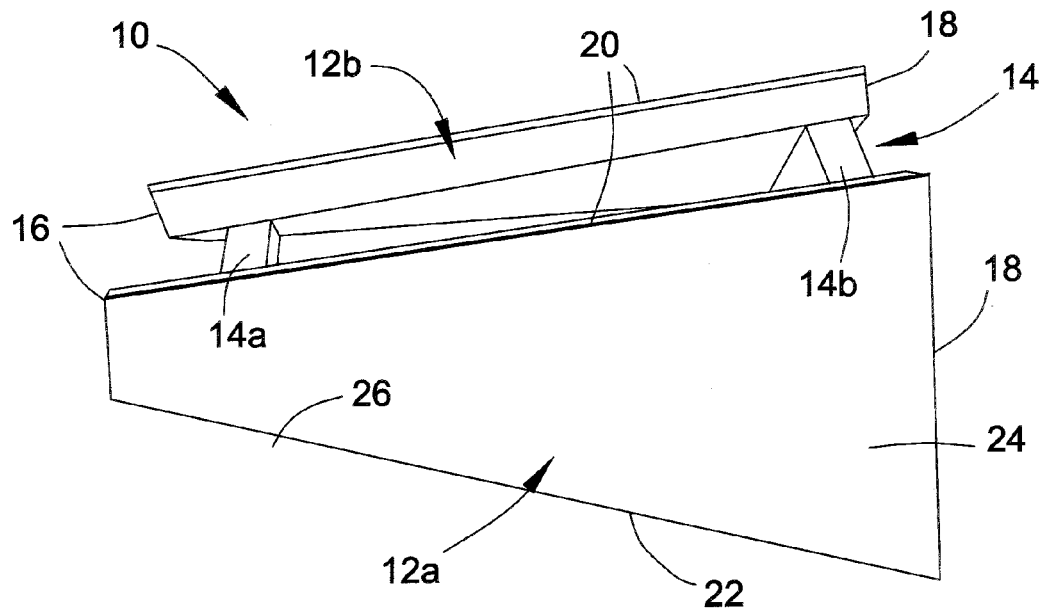

FIGS. 1 and 2 represent a freestanding Achilles tendon stretching device 10 in accordance with a first embodiment of this invention. The device 10 is shown as having wedge portions 12 comprising a left wedge portion 12a and a right wedge portion 12b, which are essentially mirror images of each other. The wedge portions 12 are shown coupled to each other through a base portion 14 that comprises two risers 14a and 14b located adjacent heel and toe ends 16 and 18, respectively, of the wedge portions 12. The heel and toe ends 16 and 18 are oppositely-disposed in the fore-aft direction of their respective wedge portions 12. Each wedge portion 12 is further configured to have oppositely-disposed inside-foot and outside-foot edges 20 and 22 in a lateral direction of the wedge portion 12, and an upper surface 24 delineated by the heel and toe ends 16 and 18 and the inside-foot and outside-foot edges 20 and 22.

The upper surface 24 of each wedge portion 12 is shown to lie in a plane but have a nonuniform elevation relative to the base portion 16 as a result of the size and shape of the risers 14a and 14b. In particular, the riser 14a adjacent the heel ends 16 of the wedge portions 12 is smaller than the riser 14b adjacent the toe ends 18 of the wedge portions 12, causing the wedge portions 12 to taper in both the fore-aft and lateral directions relative to a surface 26 on which the base portion 14 is supported, such that the inside-foot edge 20 has an increasing elevation toward the toe end 18, while the outside-foot edge 22 has a substantially constant elevation in the fore-aft direction. In addition, each wedge portion 12 has a nonconstant lateral width in the lateral direction as a result of the toe end 18 having a width that is greater than the width at the heel end 16. For example, the lateral width of each wedge portion 12 can nominally conform to a typical difference in the width of a human foot at the toes and heel. For this purpose, each wedge portion 12 may be sized for a specific range of foot sizes.

According to a preferred aspect of the invention, the fore-aft and lateral tapers of the wedge portions 12 are sufficient so that placement of one's foot on one of the upper surfaces 24 of the wedge portions 12 causes supination and locking of the foot and enables stretching of the Achilles complex. As an example, the inside-foot edge 20 at the toe end 18 may be elevated about one to about four inches (about 2.5 to about 10 centimeters) above the outside-foot edge 22 as a result of the fore-aft and lateral tapers of each wedge portion 12. As evident from FIGS. 1 and 2, the elevation of the inside-foot edge 20 relative to the outside-foot edge 22 can be achieved with the outside-foot edge 22 located at the same level as the surface 26 supporting the device 10. Alternatively, it is foreseeable that the outside-foot edge 22 could be slightly elevated at the toe end 18 relative to the heel end 16.

In use, an individual can utilize either or both wedge portions 12 of the device 10. In either case, a user places his or her heel against the upper surface 24 at the heel end 16 of the wedge portion 12 and places his or her toes against the upper surface 24 at the toe end 18 of the wedge portion 12 to cause supination and locking of the foot and stretching of the Achilles complex. In the embodiment of FIGS. 1 and 2, in which the device 10 is resting on the support surface 26, the user is able to shift his or her weight to the foot to cause weight-bearing stretching of the Achilles complex. Though shown as mirror images of each other to achieve a similar stretching effect for each foot, the fore-aft and lateral tapers of the wedge portions 12a and 12b could differ to achieve a different degree of stretching for the left and right feet.

While each wedge portion 12 is specifically configured for stretching the Achilles complex of either the right or left foot, each wedge portion 12 can also be used on the foot opposite the intended foot to pronate the opposite foot and stretch the arch of that foot, for example, as a therapeutic treatment for high arched feet.

Various materials can be used in the construction of the device 10 shown in FIGS. 1 and 2, including but not limited to plastic, rubber, metal and wood materials and combinations thereof. Though represented as an assembly of individual components, the device 10 could be produced as a unitary body, such as by a molding process that results in the device 10 being a solid body whose lower part defines the base portion 14 and whose upper part defines the wedge portions 12a and 12b and their surfaces 24. The upper surface 24 of each wedge portion 12 can be defined by or covered by a slip-resistant material, or otherwise treated to have a slip-resistant surface texture (not shown). In addition or alternatively, the device 10 can be equipped with straps 28 or other means for individually securing the user's foot or feet to the wedge portions 12.

The embodiments of FIG. 3 through 8 share similarities with the embodiment of FIGS. 1 and 2, and therefore the following discussion of the remaining embodiments will focus primarily on aspects of these embodiments that differ from the first embodiment in some notable or significant manner. Other aspects of the additional embodiments not discussed in any detail can be, in terms of structure, function, materials, etc., essentially as was described for the first embodiment.

In the embodiment of FIGS. 3 through 8, one wedge portion 12 is represented as being a separate freestanding body that, while capable of being a mirror image of a second wedge portion (not shown), is not coupled to a second wedge portion. Furthermore, the wedge portion 12 and base portion 14 of the device 10 are formed as a unitary body, and the nonuniform elevation of the upper surface 24 of the wedge portion 12 relative to the base portion 14 is the result of the wedge portion 12 having a nonuniform thickness defined by its fore-aft and lateral tapers. The wedge portion 12 of FIGS. 3 through 8 is well suited for being formed by molding, preferably from a hard plastic or rubber material. Though not shown, the embodiment illustrated in FIG. 3 can be secured to the foot with a strap similar to the embodiment of FIGS. 1 and 2, or secured in any other suitable manner such as with tape or bandage.

Figure 3:
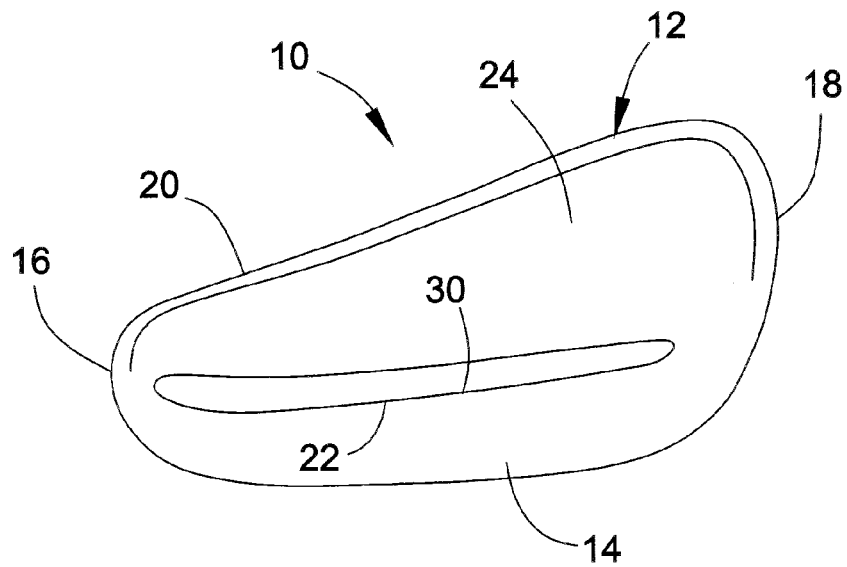
FIG. 3 is a perspective view of a freestanding Achilles tendon stretching device in accordance with a second embodiment of this invention.

As evident from FIG. 3, the elevation of the inside-foot edge 20 relative to the outside-foot edge 22 is achieved with the outside-foot edge 22 being at level above the surface 26 supporting the device 10. To promote the retention of the foot on the upper surface 24, a raised lip 30 is shown as being defined along the outside-foot edge 22. Use of the device 10 shown in FIG. 3 can be similar to that described for the embodiment of FIGS. 1 and 2. In particular, the device 10 can be used as a freestanding structure, in which case a user is able to place his or her heel against the upper surface 24 at the heel end 16 of the wedge portion 12, place his or her toes against the upper surface 24 at the toe end 18 of the wedge portion 12 to cause supination and locking of the foot, and then shift his or her weight to the foot to cause weight-bearing stretching of the Achilles complex. Similar to the embodiment of FIGS. 1 and 2, though the wedge portion 12 is specifically configured for stretching the Achilles complex of either the right or left foot, the wedge portion 12 can also be used to pronate the opposite foot for the purpose of stretching the arch of that foot.

Figure 4:
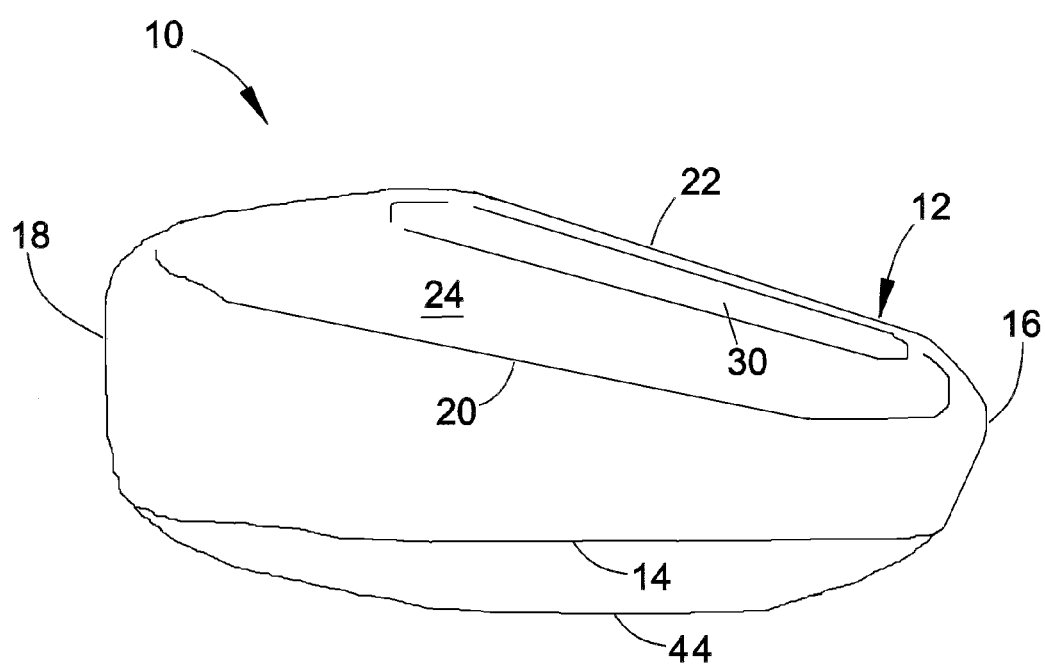
FIG. 4 is a side view of a freestanding Achilles tendon stretching device similar to FIG. 3, but with the addition of a rocker feature at its lower surface.

FIG. 4 shows an optional feature of the invention, in which the wedge portion 12 is equipped with a rocker feature 44 that can increase the stretching motion further by allowing the wedge portion 12 to be pitched fore and aft. The rocker feature 44 can be formed integrally with the base portion 14, such that the lower surface of the base portion 14 defines the rocker feature 44. Another option is to form the rocker feature 44 as a discrete accessory that can be attached to the lower (flat) surface of the base portion 14.

Figure 5:
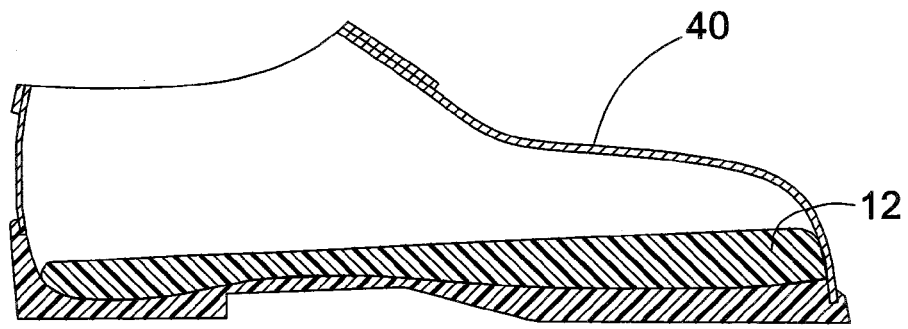
FIGS. 5, 6, 7 and 8 show the device of FIG. 3 in combination with shoes (FIGS. 5 and 6), a splint (FIG. 7), and straps (FIG. 8) in accordance with additional embodiments of the invention.
Figure 6:
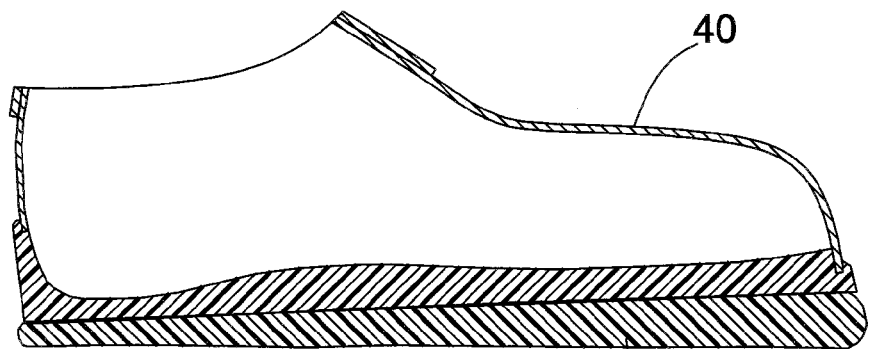
Figure 7:
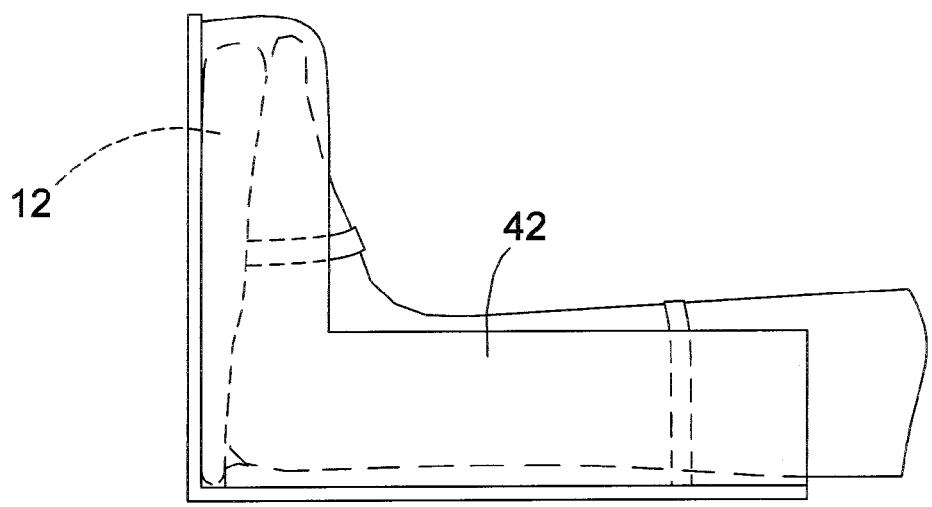

FIGS. 5 and 6 show alternative applications for the wedge portion 12 of FIG. 3 in which the wedge portion 12 is sized for placement in a shoe 40 (FIG. 5) or as an integral or attachable portion for the sole of a shoe 40 (FIG. 6). In either case, as a result of the wedge portion 12 being combined with a shoe 40, the user can don the shoe 40 to cause supination and locking of the foot, and then walk in the shoe 40 to cause weight-bearing stretching of the Achilles complex.

Figure 8:
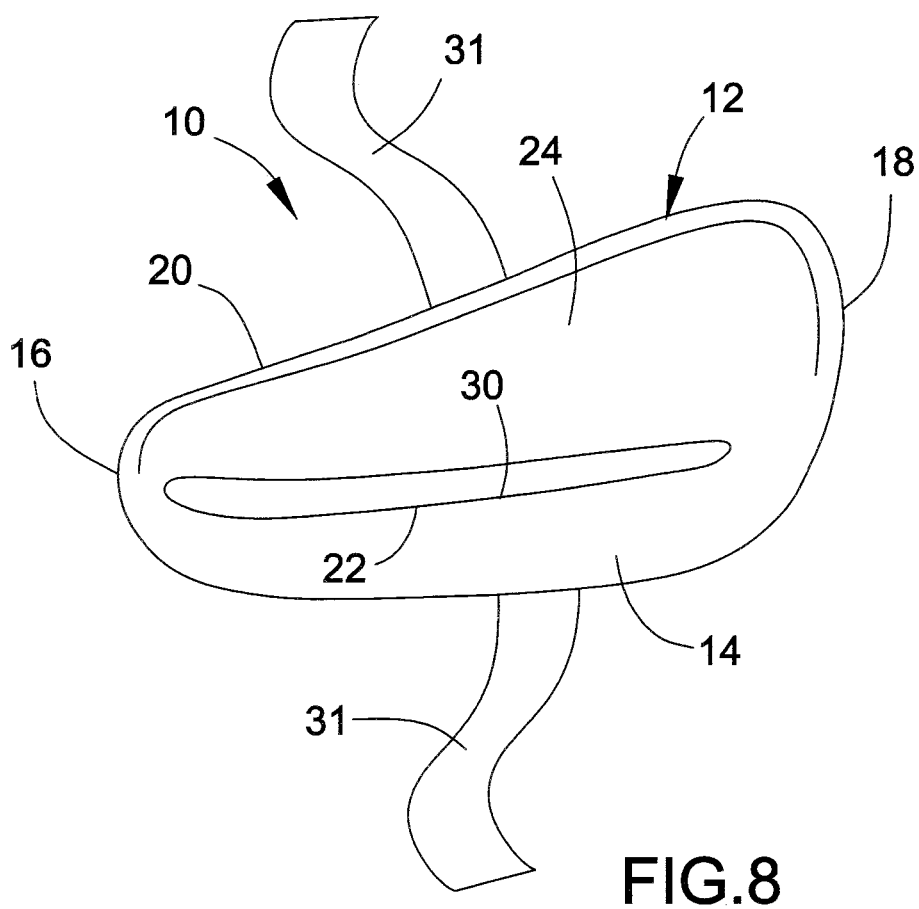

Alternatively, the device 10 can be used in combination with a leg splint 42 (FIG. 7), in which case the nonconstant elevation of the surface 24 of the wedge portion 12 can be achieved as a result of the splint 42 serving as all or part of the base portion 14 to cause twisting of the wedge portion 12 to induce supination of the foot on which the splint 42 is installed and, as a result, continuous stretching of the Achilles tendon of that foot. Still another option for the device 10 of FIG. 3 is shown in FIG. 8, in which straps 31 are shown attached to the device 10 and whose ends can be grasped and pulled by a user to twist the wedge portion 12 to induce supination of the foot and cause stretching of the Achilles tendon of that foot. Finally, as with the embodiments of FIGS. 1 through 4, the wedge portions 12 of FIGS. 5 through 8 can also be used to pronate the foot opposite the intended foot for the purpose of stretching the arch of that foot.

Figure 9:
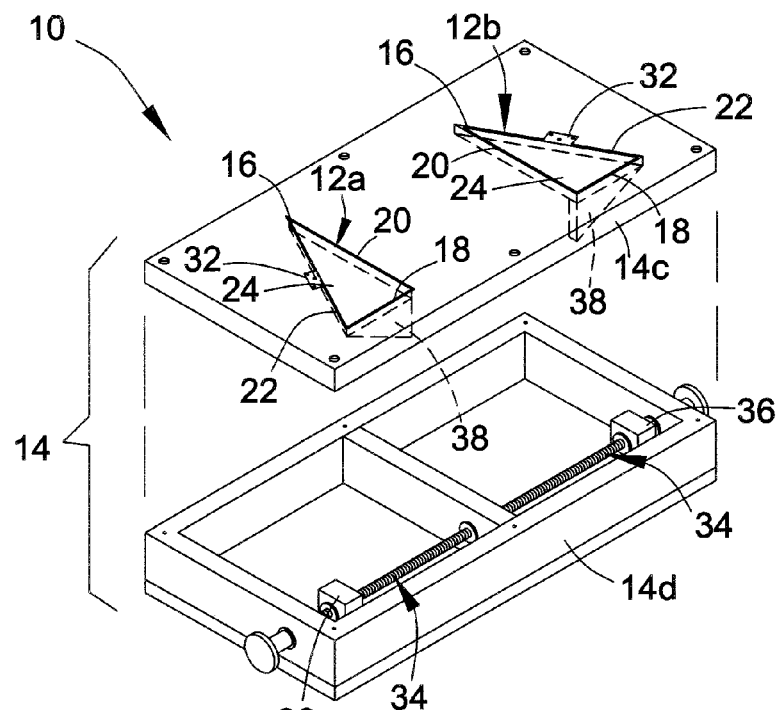
FIGS. 9 through 11 are various views of an Achilles tendon stretching device and its components in accordance with a third embodiment of this invention.
Figure 10:
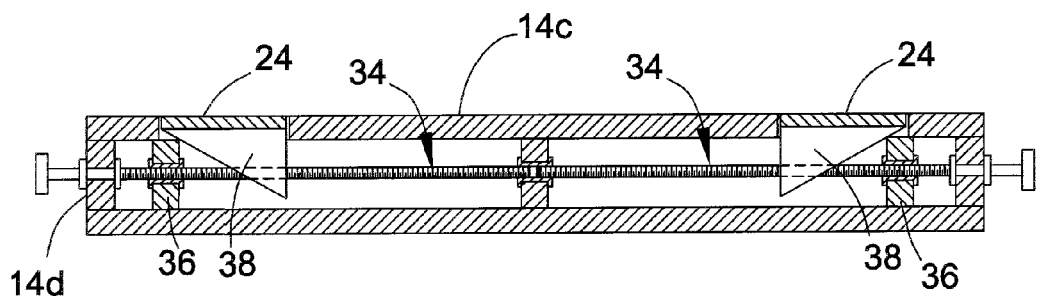
Figure 11:
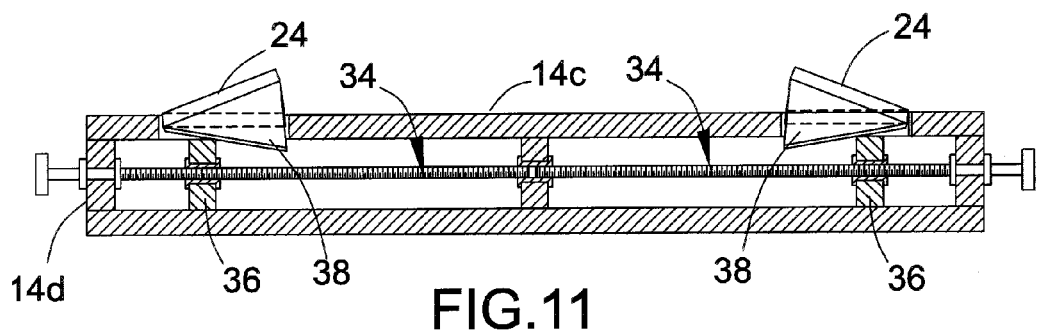

FIGS. 9 through 11 represent another embodiment of the invention in which the device 10 is a freestanding structure and the wedge portions 12a and 12b are coupled together by the base portion 14. This embodiment provides the additional capability of adjusting the elevations of the surfaces 24 of the wedge portions 12a and 12b relative to the base portion 14 through an adjustment feature built into the base portion 14. This capability enables the device 10 to allow a user to tailor the degree of stretching to meet his/her flexibility.

The wedge portions 12a and 12b are shown in FIGS. 9 to 11 as pivotably attached to the base portion 14, such as with hinges 32 either assembled to or formed integrally with the wedge portions 12a and 12b and base portion 14. The hinges 32 are located at the outside-foot edge 22 of each wedge portion 12a and 12b, while the remaining perimeter of each wedge portion 12a and 12b (defined by the heel and toe ends 16 and 18 and the inside-foot edge 20) is not coupled to the base portion 14. The wedge portions 12a and 12b have the lateral taper ascribed to the prior embodiments, though more so as the upper surface 24 of each wedge portion 12a and 12b is essentially triangular-shaped. The base portion 14 is represented as constructed of a face plate 14c attached to a frame 14d. The frame 14d provides the structural support for a pair of threaded rod and nut assemblies 34, by which rotation of each rod causes its corresponding nut to move linearly. As evident from FIGS. 9 to 11, an abutment member 36 is attached to each nut, such that rotation of the rod also causes the abutment member 36 to move linearly. Each rod and nut assembly 36 is oriented transverse to the fore-aft directions of the wedge portions 12a and 12b, which have tapered rails 38 that extend downward therefrom into the enclosure defined by the frame 14d. The rails 38 and abutment members 36 are sized and arranged so that each abutment member 36 can be linearly moved by a rod and nut assembly 34 into engagement with its rail 38 to cause the corresponding wedge portion 12a/12b to pivot relative to the base portion 14 and increase the elevation of its upper surface 24 relative to the base portion 14. It should be apparent from FIG. 9 that the rod and nut assemblies 34 and the rails 38 they engage could be oriented parallel to the fore-aft directions of the wedge portions 12a and 12b and still be capable of elevating and lowering the wedge portions 12a and 12b. Furthermore, it should be noted that other actuation mechanisms could be used in place of the rod and nut assembly 36, including pistons, expanders, jacks, and rack and pinion mechanisms.

Figure 12:
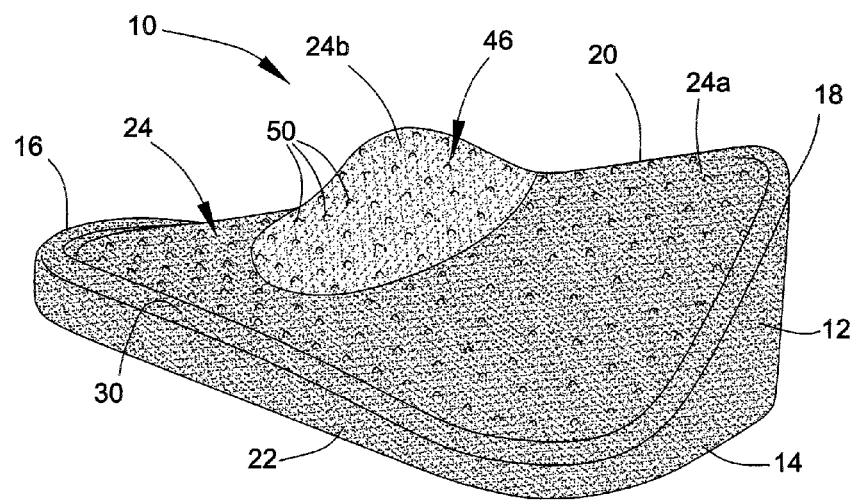
FIGS. 12 through 14 represent a perspective view and two side views of an Achilles tendon stretching device in accordance with a fourth embodiment of this invention.
Figure 13:
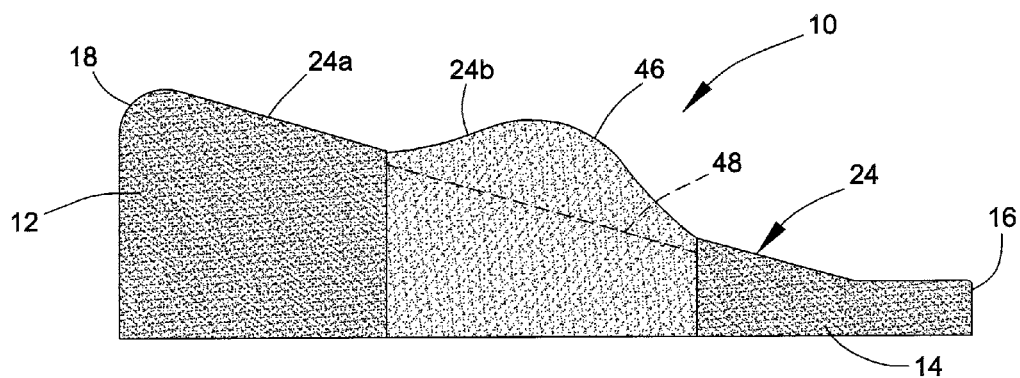
Figure 14:
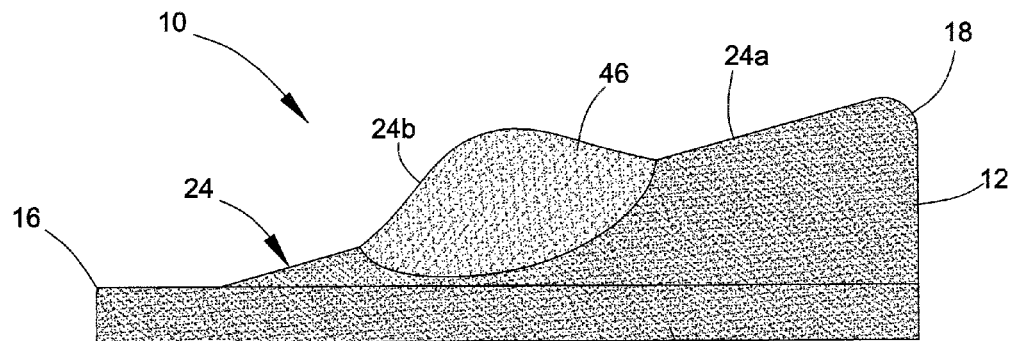
Figure 17:
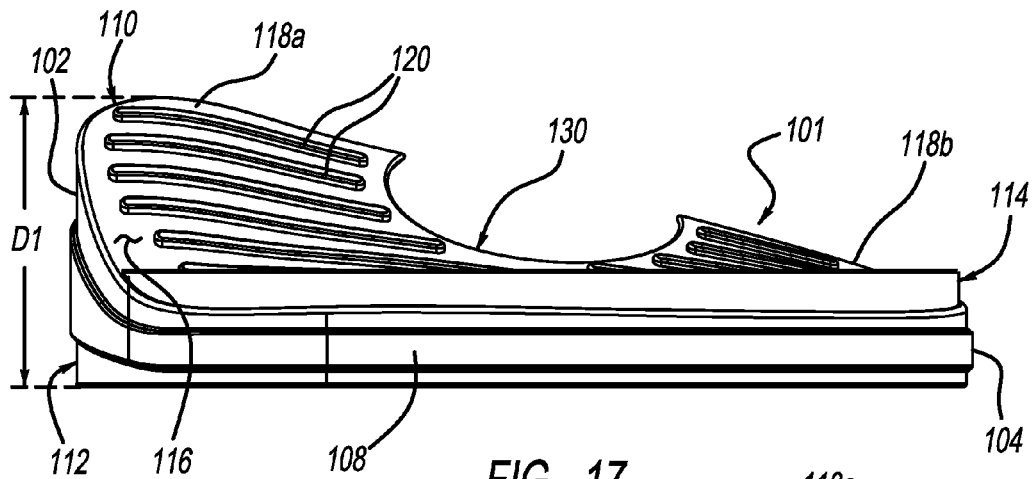
FIG. 17 is a side view of a first side of the therapeutic device of FIG. 15.

The embodiment of FIGS. 12 through 14 is represented as a separate freestanding body similar to that shown and described in reference to FIG. 3, but with the further inclusion of a projection 46 disposed on the upper surface 24 of the wedge portion. From the following, it should be understood that the projection 46 and additional features discussed below in reference to FIGS. 12 through 14 can be employed with any of the embodiments shown in FIGS. 1 through 11.

Similar to the therapeutic device 10 of FIG. 3, the device 10 represented in FIGS. 12 through 14 includes wedge and base portions 12 and 14, with the wedge portion 12 having oppositely-disposed heel and toe ends 16 and 18 in the fore-aft direction and oppositely-disposed inside-foot and outside-foot edges 20 and 22 in the lateral direction. Furthermore, the upper surface 24 of the wedge portion 12 is delineated by the heel and toe ends 16 and 18 and by the inside-foot and outside-foot edges 20 and 22. As with the device 10 of FIG. 3, the upper surface 24 comprises a planar surface portion 24a that lies in a wedge plane 48. However, due to the presence of the projection 46, the device 10 of FIGS. 12 through 14 further comprises an arcuate surface portion 24b defined by the projection 46. The projection 46 and its arcuate surface portion 24b extend out of the wedge plane 48, as particularly evident from FIG. 13. As with the upper surface 24 of the prior embodiments, the planar surface portion 24a lying in the wedge plane 48 has a nonuniform elevation relative to the base portion 14 as a result of the wedge portion 12 having a fore-aft taper in the fore-aft direction and a lateral taper in the lateral direction, such that the inside-foot edge 20 has a higher elevation at the toe end 18 than at the heel end 16. In contrast, the outside-foot edge 22 can have a substantially constant elevation in the fore-aft direction.

As seen in FIG. 12, the projection 46 extends from the inside-foot edge 20 toward but not to the outside-foot edge 24 in the lateral direction, and extends between but not to the heel and toe ends 16 and 18 of the wedge portion 12, essentially placing the projection 46 at a location corresponding to the arch of a user's foot. In a preferred embodiment, the projection 46 extends up to about 6.5 centimeters, more preferably about 4.5 to about 6.5 centimeters, from the inside-foot edge 20 toward the outside-foot edge 24 in the lateral direction, and extends about 9 to about 11 centimeters, for example about 10 centimeters, along the inside-foot edge 20 in the fore-aft direction. Furthermore, the projection 46 may be spaced a distance of about 8 to about 9.5 centimeters, more preferably about 9 centimeters, from both the heel and toe ends 16 and 18.

The arcuate surface portion 24b defined by the projection 46 is intended to correspond to the size, shape and location of the arch of a human foot. As such, the projection 46 can be seen in FIGS. 12 through 14 to define continuous arcuate contours in both the lateral and fore-aft directions of the wedge portion 12, terminating at the planar surface portion 24a or the inside-foot edge 20. These arcuate contours can be, for example, sinusoidal or parabolic in shape. To provide adequate support for the arch, the contours of the surface portion 24b preferably define an apex that is at least ten millimeters, for example, about ten to about forty millimeters, from the wedge plane 48. FIGS. 12 through 14 represent the apex as located at the inside-foot edge 20, generally consistent with the shape and location of the arch of a human foot. The surface of the surface portions 24a and 24b are represented as including small raised features 50, which can be configured to provide a slip-resistant surface texture or serve as acupuncture bumps.

Though represented as adapted to accommodate only one foot (for illustrative purposes, FIGS. 12 through 14 depict a right-footed device 10), the device 10 could be readily configured to accommodate both feet, as shown in FIGS. 1, 2 and 9-11 and as previously discussed in reference to FIG. 3, in which case the device 10 would further include a second wedge portion and projection that are preferably mirror images of the wedge portion 12 and projection 46 shown in FIGS. 12 through 14. The projection 46 is represented in FIGS. 12 through 14 as integrally formed with the remainder of the device 10, for example, part of a freestanding body formed as a one-piece molding of a hard plastic or rubber material. As a result, the projection 46 may have a fixed shape and height. Alternatively, the projection 46 could be a removable feature allowing projections 46 of different shapes and heights to be installed on the upper surface 24 of the wedge portion 12. Furthermore, the projection 46 could be configured so that its height and shape is adjustable. For example, the projection 46 could be a hollow feature that allows its shape and height to be altered by injecting air or another suitable fluid (liquid or gas) into a cavity located beneath the surface portion 24 b, for example, between the surface portion 24b and the wedge plane 48. In addition, the projection 46 could be adjusted by various other means, for example, with a jack and pinion, Consistent with the prior embodiments, the fore-aft and lateral tapers of the wedge portion 12 are sufficient so that placement of a user's foot against the upper surface 24 of the wedge portion 12 causes supination and locking of the foot to enable stretching of the Achilles complex. More particularly, the user's heel is supported at the heel end 16 by the planar surface portion 24a, and the user's toes are supported at the toe end 18 by the planar surface portion 24a. Additionally, the arch of the user's foot is against and supported by the arcuate surface portion 24b between the heel and toe ends 16 and 18 of the wedge portion 12, with the result that the projection 46 at least minimizes if not avoids stretching of the arch of the foot while a user stretches their calf muscles and Achilles tendon with the device 10. As such, the device 10 represented in FIGS. 12 through 14 is capable of avoiding the creation or worsening of a flatfoot condition.

With reference to FIGS. 15 through 27, another configuration of a therapeutic device 100 is shown. The structure and function of the therapeutic device 100 may be substantially similar to that of the therapeutic device 10 illustrated in FIGS. 1 through 14, apart from any exceptions described below and/or shown in the Figures. Therefore, the structure and/or function of similar features will not be described again in detail, and like reference numerals may be used to describe like features and components.

The device 100 may include a base 101 and an insert 103. The base 101 may be formed from an elastomeric or otherwise flexible material, and may include a first end 102, a second end 104, a first side 106 and a second side 108. The first end 102 may be a front or toe end of the base 101, and the second end 104 may be a rear or heel end of the base 101. Likewise, the first side 106 may be an inner-foot side of the base 101, and the second side 108 may be an outer-foot side of the device.

The base 101 may further include an upper or tread portion 110, a lower or base portion 112, and a rim portion 114. In one configuration, the tread, base and rim portions 110, 112, 114 may be monolithically formed, and adapted to receive the user's foot. Specifically, the tread and base portions 110, 112 may extend from and between first and second ends 102, 104, and from and between the first and second sides 106, 108. In this regard, the tread and base portions 110, 112 may be sized and shaped to accommodate a wide range of human foot sizes. For example, in one configuration, the tread and base portions 110, 112 may be sized and shaped to receive men's shoe sizes in the range from six to thirteen.

Figure 18:
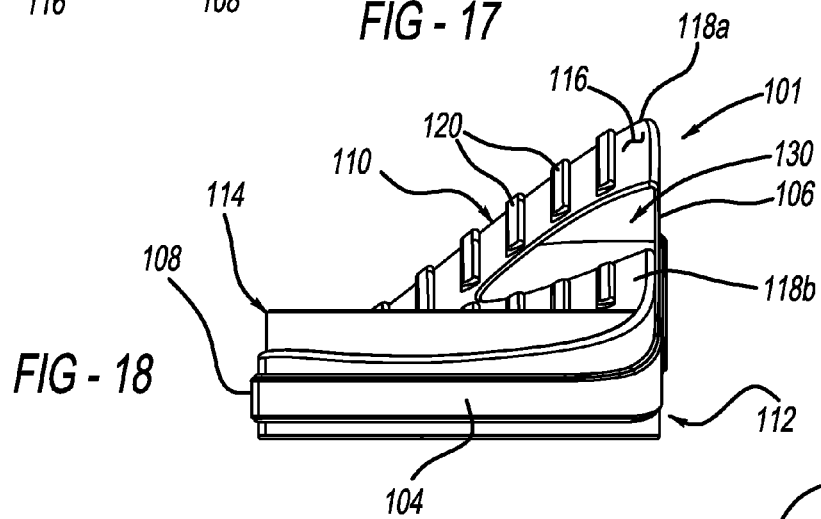
FIG. 18 is an end view of a first end of the therapeutic device of FIG. 15.
Figure 19:
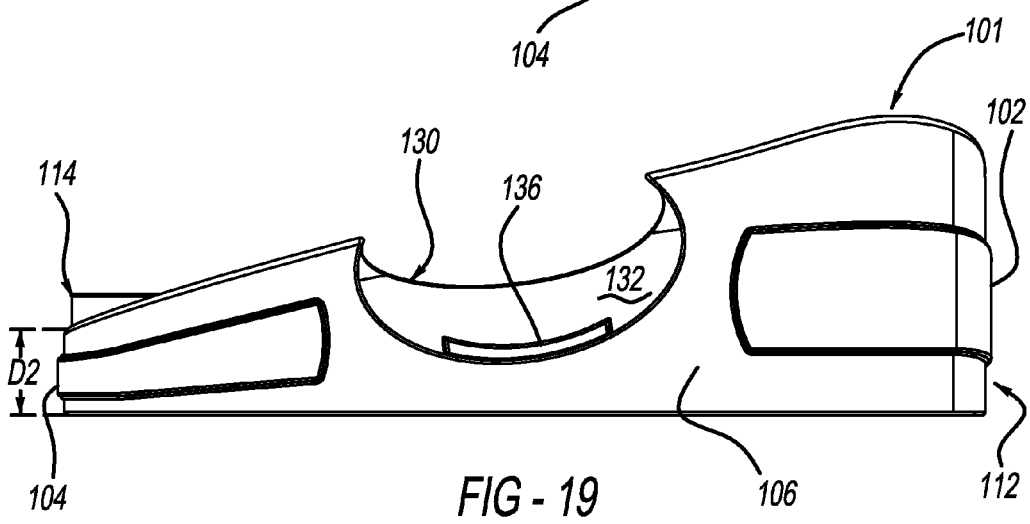
FIG. 19 is side view of a second side of the therapeutic device of FIG. 15.
Figure 20:
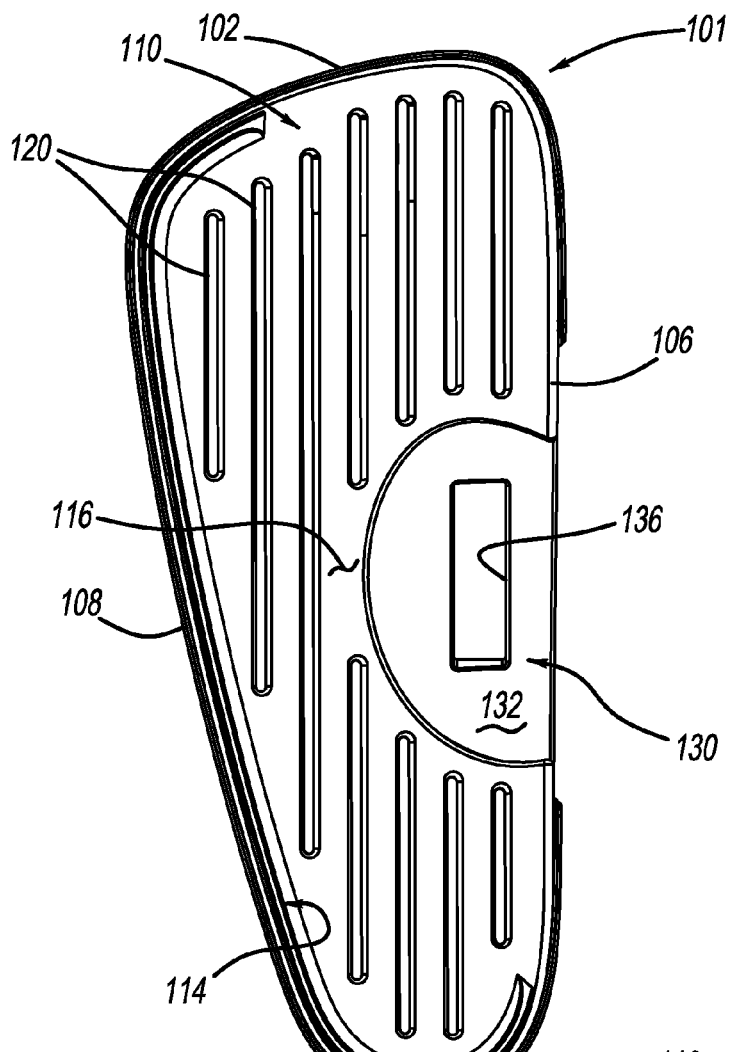
FIG. 20 is a top view of the therapeutic device of FIG. 15.
Figure 21:
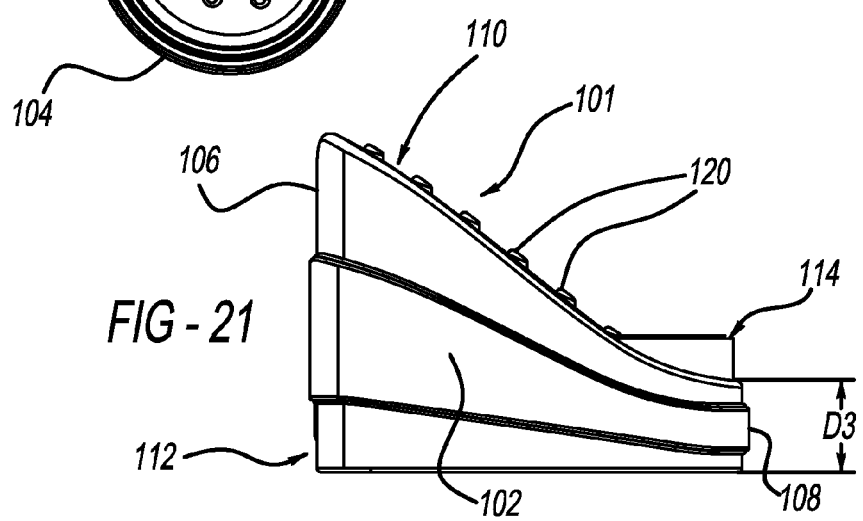
FIG. 21 is an end view of a second end of the therapeutic device of FIG. 15.

The tread portion 110 may include an upper or foot support surface 116. The foot support surface 116 may be contoured, including various concave and/or convex portions to conform to a sole of the user's foot. For example, as illustrated in FIGS. 16 and 18, the foot support surface 116 may include a first convex portion 118a proximate the first end 102 of the base 101 and a second convex portion 118b proximate the second end 104 of the base 101.

A plurality of longitudinal treads or protrusions 120 may project from the foot support surface 116 of the base 101. As illustrated, the protrusions 120 may be formed parallel to one another and generally extend between the first and second ends 102, 104 of the base 101, such that the protrusions 120 help to grip or otherwise secure the user's foot relative to the base 101. In this regard, the foot support surface 116 may also include a molded texture (e.g., a rough or otherwise roughened surface 116) that further serves to provide traction to the foot during stretching, thereby helping to secure the user's foot relative to the base 101.

With reference to FIGS. 22 and 27, the base portion 112 may extend from the tread portion 110. In this regard, the base portion 112 may include a plurality of intersecting ribs or partitions 122 extending from the tread portion 110. As illustrated, in one configuration, the base portion includes an array of orthogonally intersecting partitions 122, such that the partitions 122 define a grid, including a plurality of chambers 124. The construction and configuration of the partitions 122 and the chambers 124 can help to reduce the amount of scrap material produced during the manufacturing process, while also reducing the weight and material cost of the base 101. In this regard, it will be appreciated that the partitions 122 may include a plurality of C-shaped notches (not shown) that can allow the base 101 to form evenly during an injection molding manufacturing process, while preventing short shots. It will be appreciated that the configuration of the partitions 122 can provide a sturdy base structure capable of supporting at least three hundred pounds of weight applied in a downward direction (relative to the view in FIGS. 18 and 19).

The partitions 122 may extend from and between a proximal end 126 and a distal end 128. The proximal end 126 of each partition 122 may be adjacent to, and integrally formed with, the tread portion 110. The distal end 128 of the partitions 122 may collectively define a plane, such that the partitions 122, including the distal ends 128 thereof, can be placed on, or otherwise supported by, a substantially flat surface, such as a floor or the ground. The partitions 122 may extend various distances, or lengths, between the proximal and distal ends 126, 128, thereof. As illustrated, in one configuration, the distance between the proximal and distal ends 126, 128 of each partition 122 varies such that the foot support surface 116 and the distal ends 128 of the partitions 122 define a substantially wedge-shaped base 101. In this regard, a distance D1 between the proximal and distal ends 126, 128 of the partitions 122 located near the first end 102 of the base 101 may be greater than a distance D2 between the proximal and distal ends 126, 128 of the partitions located near the second end 104 of the device. Similarly, a distance D3 between the proximal and distal ends 126, 128 of the partitions 122 located near the second side 108 of the base 101 may be greater than a distance D4 between the proximal and distal ends 126, 128 of the partitions located near the first side 106 of the device.

The rim portion 114 of the base 101 may project from the foot support surface 116, generally proximate or adjacent to the second side 108. As illustrated in FIG. 26, in one configuration, the rim portion 114 extends from and between the first and second ends 102, 104 of the base 101, generally along the second side 108. In this regard, portions of the rim portion 114 may extend along the first and second ends 102, 104, such that the rim portion 114 defines a peripheral wall of the base 101. Accordingly, the rim portion 114 can help to secure the user's foot to the base 101, or otherwise prevent the user's foot from moving from the first end 102 to the second end 104 and/or from moving from the first side 106 to the second side 108 relative to the foot support surface 116.

The base 101 may also include a cavity or recess 130 defined by a surface 132. The recess 130 may be aligned with the arch of the user's foot. In this regard, the recess 130 may be formed in both the foot support surface 116 and the first side 106 of the base 101, such that the surface 132 includes a concave contour.

The surface 132 may include a through-hole or aperture 136. The aperture 136 may be aligned with at least one of the chambers 124 defined by the partitions 122. In this regard, opposing partitions 122a and 122b may each include a flanged portion 138 defining a stop surface 140. The stop surface 140 may generally face the distal end 128 of the partition 122.

Figure 24:
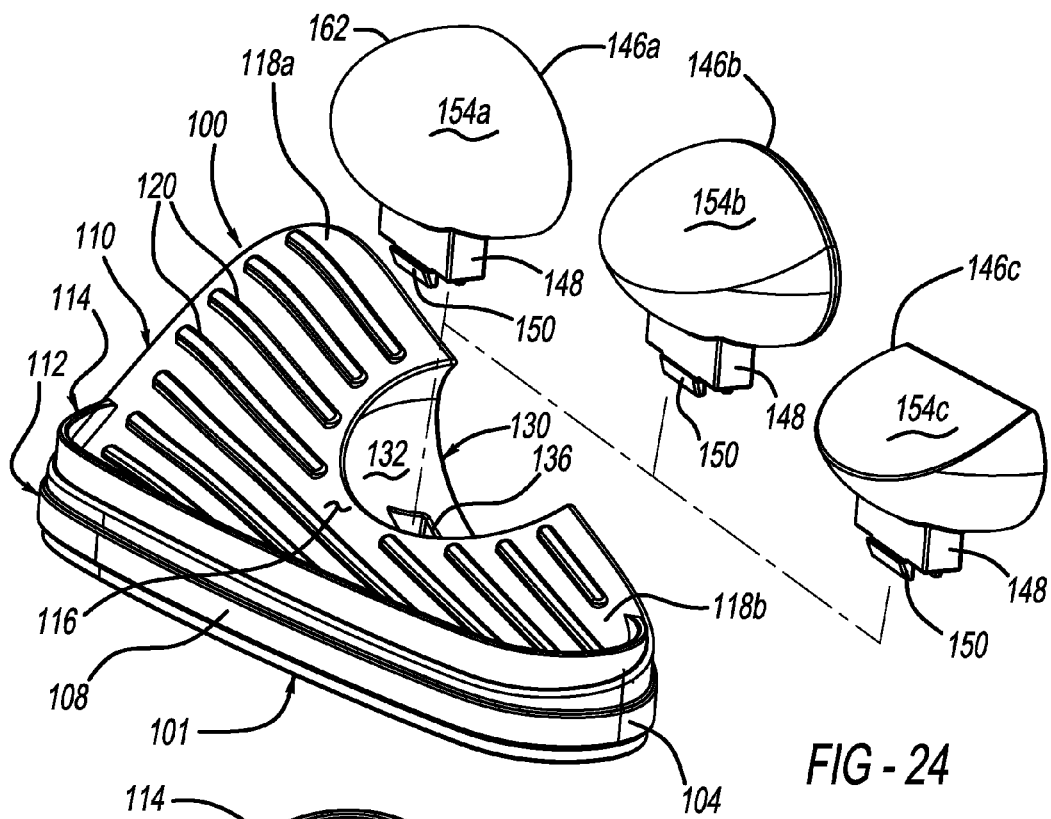
FIG. 24 is an exploded view of the therapeutic device of FIG. 15, including various configurations of an insert in accordance with the principles of the present disclosure.

With reference to FIGS. 23-27, the insert 103 may include a head portion 146 and a stem portion 148, and may be removably received by the recess 130. Specifically, the aperture 136 may be sized and shaped to receive the stem portion 148 and the recess 130 may be sized and shaped to receive the head portion 146. In one configuration, the stem portion 148 may have a substantially rectangular cross section, such that the stem portion can slide or otherwise be received within the chamber 124 and between the orthogonally intersecting partitions 122. As illustrated in FIGS. 24 and 27, the stem portion 148 may include opposed lock portions or tabs 150. The tabs 150 may be flexible such that, upon assembling the insert 103 into the base 101, the tabs 150 can lock against a portion of the partitions 122, including the stop surface 140. Locking the tabs 150 against the stop surface 140 can help to secure the insert 103 within the recess 130. To release the insert 103 from the recess 130, the user can bias the tabs 150 toward each other, such that the tabs 150 are no longer engaged with the stop surface 140, and the insert 103 can be removed from the recess 130.

As illustrated in FIG. 24, the head portion 146 of the insert 103 may include alternate configurations such that the insert 103 can be customized to fit or otherwise conform to the size and shape of different users' feet. Specifically, in a first configuration, a head portion 146a may include a surface 154a defining a convex curvature extending in at least two directions. In one configuration, the surface 154a may substantially define a portion of a sphere or an ellipsoid. In this regard, the surface 154a may be sized and shaped to conform to the sole of a foot that defines a high arch portion. In a second configuration, a head portion 146b may include a surface 154b defining a convex curvature extending in at least one direction. In this regard, the surface 154b may be sized and shaped to conform to the sole of a foot that defines a neutral or normal arch portion. In a third configuration, a head portion 146c may include a substantially planar surface 154c. In this regard, the surface 154c may be sized and shaped to conform to the sole of a foot that defines a low arch portion, or substantially flat foot. While three configurations of the insert 103 are illustrated, it will be appreciated that the insert 103 may include more than three configurations within the scope of the present disclosure, such that the base 101 and the insert 103 can accommodate various foot shapes. Thus, the various configurations of the insert 103 may define varying distances from an apex 162 of the insert 103 (e.g., an apex 162 of the surface 154a) to the distal end 128 of the partitions 122. It will also be appreciated that the various inserts 103 may be coded (e.g., color coded) to indicate the particular configuration of the surface 154.

Figure 25:
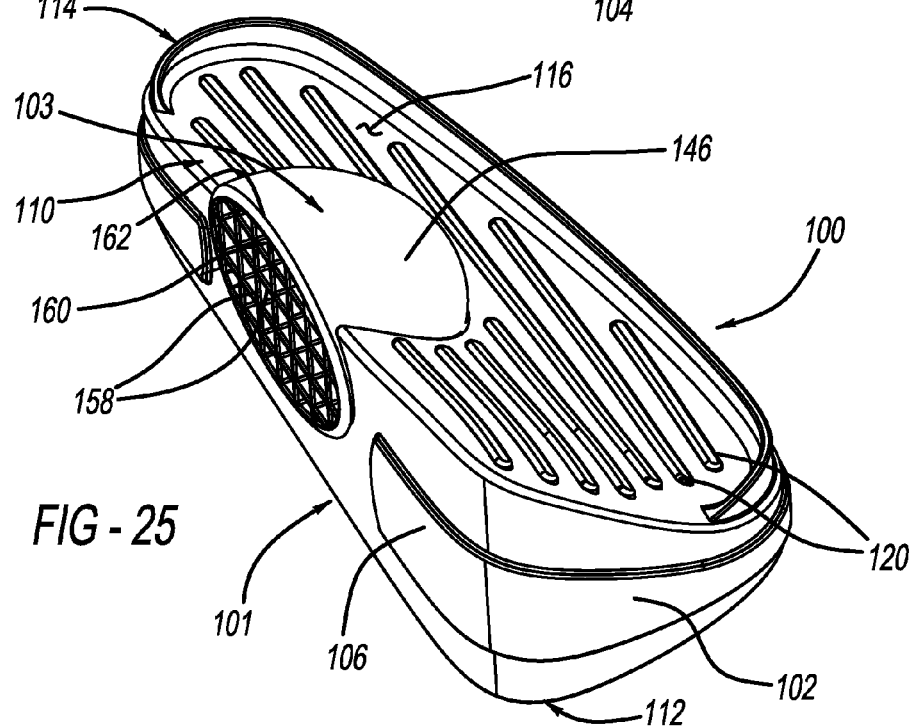
FIG. 25 is a perspective view of the therapeutic device of FIG. 23.

With reference to FIG. 25, an inner portion 156 of the head portion 146 may include a plurality of intersecting ribs or partitions 158. As illustrated, in one configuration, the inner portion 156 includes an array of orthogonally intersecting partitions 158, such that the partitions 158 define a grid, including a plurality of chambers 160. The partitions 158 can help to maximize the structural rigidity of the head portion 146, while concurrently reducing the overall cost and weight of the insert 103.

A first method of using the device 100 may include placing the user's foot on the foot support surface 116. In one configuration, an outer side of the user's foot may be aligned with, and adjacent to, the rim portion 114, an arch portion or inner side of the user's foot may be aligned with the recess 130 and the insert 103, and the heel of the user's foot may be aligned with the second end 104 of the device 100. In this particular configuration, the device 100 may be particularly well suited for stretching the user's calf and Achilles tendon. The user's calf may be effectively stretched when the user's foot is locked, or otherwise defines a high arch. Accordingly, if the user has a flat foot (i.e., a low arch or no arch), the inserts 103 may be used in a graduated manner to create a flexible arch. Once the user's arch is sufficiently flexible, the user's foot will successfully lock in a high arch position to allow for effective calf stretching. In this regard, the graduated method of using the device 100 may include first using the insert 103 defining the substantially planar surface 154c, or first using the insert 103 having the surface 154b that is sized and shaped to conform to the sole of a foot that defines a neutral or normal arch. The graduated method may thereafter include using the arch 103 having the surface 154b that is sized and shaped to conform to the sole of a foot that defines a neutral or normal arch, and/or further using the arch 103 having the surface 154a that is sized and shaped to conform to the sole of a foot that defines a high arch. In this way, a flat foot is gradually flexed to create a higher arch, which can allow the foot to lock for effective stretching of the user's calf and Achilles tendon.

A second method of using the device 100 may include placing the user's foot on the foot support surface 116 such that the inner side of the user's foot is aligned with, and adjacent to, the rim portion 114, the outer side of the user's foot is aligned with, or adjacent to, the recess 130 and the insert 103, and the heel of the user's foot may be aligned with the second end 104 of the device 100. In this regard, it will be appreciated that the first method may include placing the user's left foot on the device 100, while the second method may include placing the user's right foot on the device 100. In this particular configuration (i.e., the second method), the device 100 may be particularly well suited for stretching the user's foot. In this regard, if the user has a high arched foot, the device 100 may be used unlock the user's foot and flatten the arch. The second method may include using the insert 103 defining the substantially planar surface 154c. In this way, a high arched, or locked, foot is gradually flexed to create a lower arch, which can help to alleviate various problems associated with a high arched foot, such as sprained and fractured ankles, foot stress fractures, calluses and foot pain.

While the invention has been described in terms of specific embodiments, it is apparent that other forms could be adopted by one skilled in the art. For example, the physical configuration of the wedges and foot plates could differ from that shown, and materials and processes other than those noted could be used. Therefore, the scope of the invention is to be limited only by the following claims.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A therapeutic device for a leg or a foot, the device comprising:
    a base having a foot support surface extending from and between an elevated first toe end and a lower second heel end as compared to said first end, and extending from and between an elevated first medial side and a lower second lateral side as compared to said elevated first side, the foot support surface sloping continuously downwardly from said first end to said second end and from said first side to said second side and having a recess located along said first side, said recess including an aperture positioned within the recess; and
    an insert having a rigid head and a stem extending downwardly from said rigid head, the head removably received within the recess, and the stem portion removable received within the aperture and including at least one tab which engages said base via said aperture to releasably lock said insert to said base.

2. The therapeutic device of claim 1, wherein the base is substantially wedge-shaped, defining a varying distance between the foot support surface and a lower surface.

3. The therapeutic device of claim 1, wherein the base defines a lower surface opposite the foot support surface, the lower surface and the foot support surface defining a first distance, a second distance, and a third distance therebetween, wherein the first distance is proximate the first end, the second distance is proximate the second end, and the third distance is proximate the second side.

4. The therapeutic device of claim 1, wherein the base includes a base portion having a plurality of intersecting partitions.

5. The therapeutic device of claim 4, wherein the partitions define a plurality of chambers therebetween.

6. The therapeutic device of claim 1, wherein the base includes a peripheral rim projecting from the foot support surface.

7. The therapeutic device of claim 6, wherein the peripheral rim includes a rim portion which extends from and between the first and second ends of the base, generally along the second side.

8. The therapeutic device of claim 1 wherein said insert includes a plurality of inserts of varying size and shape.

* * * * *